United States Patent
Mori et al.

(10) Patent No.: US 8,257,564 B2
(45) Date of Patent: Sep. 4, 2012

(54) GAS SENSOR, AND GAS SENSOR MANUFACTURING METHOD

(75) Inventors: Kentaro Mori, Komaki (JP); Koji Shiono, Komaki (JP)

(73) Assignee: NGK Spark Plug Co., Ltd., Nagoya-shi (JP)

( * ) Notice: Subject to any disclaimer, the term of this patent is extended or adjusted under 35 U.S.C. 154(b) by 1232 days.

(21) Appl. No.: 11/288,372

(22) Filed: Nov. 29, 2005

(65) Prior Publication Data

US 2006/0113188 A1    Jun. 1, 2006

(30) Foreign Application Priority Data

Nov. 30, 2004    (JP) .............................. P. 2004-346331

(51) Int. Cl.
*G01N 27/407*    (2006.01)
(52) U.S. Cl. ........................................ 204/424; 204/428
(58) Field of Classification Search .................. 204/410, 204/411, 421–429; 205/783.5–785, 781, 205/787; 73/23.31, 23.32
See application file for complete search history.

(56) References Cited

U.S. PATENT DOCUMENTS

| | | | |
|---|---|---|---|
| 4,383,906 A * | 5/1983 | Sano et al. | 204/416 |
| 4,569,748 A | 2/1986 | Yamakawa et al. | |
| 4,626,337 A | 12/1986 | Hotta et al. | |
| 4,956,072 A | 9/1990 | Kojima et al. | |
| 5,536,574 A * | 7/1996 | Carter | 428/381 |
| 5,670,032 A * | 9/1997 | Friese et al. | 204/424 |
| 5,698,084 A * | 12/1997 | Weyl et al. | 204/424 |
| 5,795,454 A | 8/1998 | Friese et al. | |
| 5,935,399 A * | 8/1999 | Tanaka et al. | 204/424 |
| 6,565,723 B1 | 5/2003 | Danley et al. | |
| 2004/0011116 A1 | 1/2004 | Weyl et al. | |

FOREIGN PATENT DOCUMENTS

| | | |
|---|---|---|
| CN | 1128565 A | 8/1996 |
| DE | 44 00 370 A1 | 7/1995 |
| JP | 60-179862 U | 11/1985 |
| JP | 60-183857 U | 12/1985 |
| JP | 63-003250 A | 1/1988 |
| JP | 63-003252 A | 1/1988 |
| JP | 1-140055 A | 6/1989 |
| JP | 8-211013 A | 8/1996 |
| JP | 9-500729 A | 1/1997 |
| JP | 2000-502456 A | 2/2000 |
| JP | 2001-281209 A | 10/2001 |
| WO | WO 95/18964 | 7/1995 |
| WO | 98/15819 A1 | 4/1998 |

OTHER PUBLICATIONS

Chinese Office Action dated Apr. 11, 2008.

* cited by examiner

*Primary Examiner* — Alex Noguerola
*Assistant Examiner* — Gurpreet Kaur
(74) *Attorney, Agent, or Firm* — Sughrue Mion, PLLC

(57) ABSTRACT

A gas sensor comprising: a gas detecting element extending in an axial direction and including a detecting electrode provided on an outer surface of a leading end side of the gas detecting element, and a lead portion connecting to the detecting electrode and extending toward a rear end side of the gas detecting element; a cylindrical metal shell housing the gas detecting element such that the gas detecting element protrudes from a leading end side of the metal shell; a powder layer filling a gap between the gas detecting element and the metal shell and covering at least a portion of the lead portion; and an insulating layer provided between the powder layer and the lead portion. Also disclosed is a method for manufacturing the gas sensor which includes forming the insulating layer by at least: applying a glass paste; drying the glass paste; and heat-treating the glass paste.

8 Claims, 6 Drawing Sheets

GAS SENSOR, AND GAS SENSOR MANUFACTURING METHOD

BACKGROUND OF THE INVENTION

1. Field of the Invention

The present invention relates to a gas sensor for detecting a gas such as oxygen in a gas to be measured, which can be the exhaust gas of an internal combustion engine, and a method for manufacturing the gas sensor.

2. Description of the Related Art

A gas sensor, which has a bottomed cylindrical shape having its leading end closed and detecting electrodes on its inner and outer faces, is known for use in detecting a specific gas component in a gas to be measured, such as a gas sensor for detecting oxygen or the like in the exhaust gas of an internal combustion engine. In this gas sensor, the gas concentration is detected by introducing atmospheric air as a reference gas to the inner side of the gas detecting element, and by contacting the outer side with the gas to be measured. An electromotive force, developed according to the difference in gas concentration between the inside and outside of the detecting element, is measured.

In this known gas sensor, moreover, a metallic housing (or a metal shell) encloses the gas detecting element so as to support the gas detecting element at a predetermined position. A gas sensor is also known in which a powder layer is arranged between the gas detecting element and the metallic housing so as to maintain gas-tightness therebetween (as disclosed by JP-A-2001-281209, for example).

3. Problems to be Solved by the Invention

However, the gas sensors of the prior art thus far described have been found to have the following problems. Specifically, the powder layer absorbs moisture, if exposed to a humid environment (i.e., high humidity), so that there is a decrease in electrical resistance between the metallic housing and the outer electrode of the gas detecting element. As a result, an electric current flows therebetween to generate output noise, and precise gas concentration detection may be impaired.

The present invention has been conceived to solve the aforementioned problems. Therefore, an object of the present invention is to provide a gas sensor capable of maintaining requisite insulation properties even in the case where a powder layer subjected to a humid environment may absorb moisture, and to a method for manufacturing the gas sensor.

SUMMARY OF THE INVENTION

The above objects of the invention have been achieved by providing a gas sensor comprising: a gas detecting element extending in an axial direction and including a detecting electrode provided on an outer surface of a leading end side, and a lead portion connecting to said detecting electrode and extending toward a rear end side; a cylindrical metal shell housing said gas detecting element such that said gas detecting element protrudes from a leading end side of said metal shell; and a powder layer filling a gap between said gas detecting element and said metal shell and covering at least a portion of said lead portion. The gas sensor is characterized as further comprising an insulating layer provided between said powder layer and the portion of said lead portion covered by the powder layer.

The gas sensor of the invention is imparted with such structure by interposing an insulating layer between the powder layer and the portion of the lead portion, so as to prevent direct contact between the portion of the lead portion covered by the powder layer and the powder layer. As a result, the desired insulation properties can be retained even in the case where the powder layer absorbs moisture when subjected to a humid environment. As a result, such structure can prevent electric current from flowing between the metal shell and the lead portion, so as to prevent noise generation in the output and thereby provide precise gas concentration detection measurements.

The lead portion may extend over the outer circumference of the gas detecting element in a rear end direction farther than the rear end side of the powder layer. Moreover, the lead portion may be formed so as to extend over the entire circumference of the gas detecting element, or may be formed so as to extend in a rod shape in the circumferential portion of the gas detecting element toward the rear end side from the detecting electrode.

In the gas sensor of the invention, the insulating layer preferably comprises glass, and more preferably the insulating layer is mainly (e.g. not less than 80% by weight) composed of glass. The insulating layer can include some ceramic fillers made of e.g. alumina, preferably at less than 20% by weight. By providing an insulating layer comprising glass, the heat resistance can be retained while providing sufficient insulation properties.

In the gas sensor of the invention, moreover, the insulating layer preferably includes a plurality of layers. As a result, an insulating layer mainly made from glass can be formed so as to have no pores, to thereby further prevent a reduction in insulation properties due to the presence of pores.

In the gas sensor of the invention, of the plural layers, a first insulating layer adjacent to the lead portion is preferably made from crystallized glass. When the first insulating layer adjacent to the lead portion is made from crystallized glass, the first insulating layer is resistant to softening. Thus, the second insulating layer adjacent to the first insulating can be formed while maintaining the original thickness of the first insulating layer. As a result, an insulating layer having a large thickness can be formed to prevent a reduction in insulation properties.

The gas detecting element may have a flange bulging to the radially outer side, and this flange plays a role in fixing the gas detecting element to the metal shell and the insulator through the packing. In the rear end direction farther than the packing, a portion of the powder layer may enter the gap between the gas detecting element and the metal shell or the insulator. The powder layer then absorbs moisture, as described above, so that the electric resistance between the metal shell and the detecting electrode of the gas detecting element or the lead portion is lowered. As a result, electric current may flow therebetween, and noise may be introduced into the output to interfere with precise gas concentration detection.

In the gas sensor of the invention, therefore, it is preferable that the insulating layer preferably extends so far as to cover a portion of the flange contacting the packing. When the insulating layer extends so far as to cover a portion of the flange contacting the packing, a short-circuit between the metal shell and the detecting electrode or the lead portion can be prevented even if the powder layer provided at the portion of the flange contacting the packing absorbs moisture.

The gap is formed, in the leading end direction, farther than the packing between the gas detecting element and the metal shell. When the gas sensor is attached to an exhaust pipe or the like, the gap between the gas detecting element and the metal shell is exposed to the gas to be measured, so that carbon or the like in gas entering the gap adheres to the surfaces of the gas detecting element and the metal shell. The carbon also adheres to the detecting electrode or the lead portion provided in the gas detecting element. As a result, the electrical resistance between the metal shell and the detecting electrode or the lead portion of the gas detecting element is lowered to allow an electric current to flow, and noise may be introduced into the output to interfere with precise gas concentration detection.

In the gas sensor of the invention, therefore, the gas detecting element preferably includes a porous protecting layer covering at least a portion of the detecting electrode and lying over or rather overlapping at least the leading end portion of the insulating layer. On the outer circumference of the detecting electrode of the gas sensor, a protecting layer is provided for suppressing a reduction, as might otherwise be caused by a poisoning substance such as Pb in the gas to be measured, in the detecting precision of the gas sensor. By superposing the protecting layer and the insulating layer at its leading end side (that is, by covering that portion of the gas detecting element present beyond the packing in the leading end direction with the protecting layer and the insulating layer), the flow of electric current between the metal shell and the detecting element or the lead portion can be prevented by the protecting layer and the insulating layer. This is the case even if carbon or the like enters the gap between the metal shell and the gas detecting element and adheres to the metal shell and the gas detecting element This arrangement effectively prevents noise from being introduced into the output to thereby allow for precise gas concentration detection.

In the gas sensor of the invention, therefore, the protecting layer preferably covers the leading end portion of the insulating layer. The insulating layer does not readily enter into the pores of the porous protecting layer, when covered by the protecting layer, and the protecting layer may not adversely affect the insulation properties. To the contrary, the insulation properties can be maintained, as in the invention, by covering the leading end portion of the insulating layer with the protecting layer.

Moreover, the insulating layer preferably extends farther in the leading end direction than the leading end of the metal shell. As a result, even if carbon or the like adheres to the metal shell or the gas detecting element, the insulating layer can effectively prevent electric current flow between the metal shell and the detecting element or the lead portion, and prevent noise from being introduced into the output to allow for precise gas concentration detection.

According to the invention, a gas sensor manufacturing method for manufacturing the gas sensor is characterized by forming the insulating layer by applying a glass paste, drying the glass paste, and heat-treating the glass paste. One preferable mode of the gas sensor manufacturing method of the invention is characterized in that a series of steps including the above application, drying and heat treatment steps are repeated at least two times to form the insulating layer. By carrying out these steps, it is possible to form an insulating layer having sufficient thickness, insulating properties and heat resistance.

The invention, provides a gas sensor capable of maintaining good insulating properties even in the case where the powder layer is subjected to a humid environment so as to absorb moisture, and a method for manufacturing the gas sensor.

DESCRIPTION OF REFERENCE NUMERALS

Figure 1:
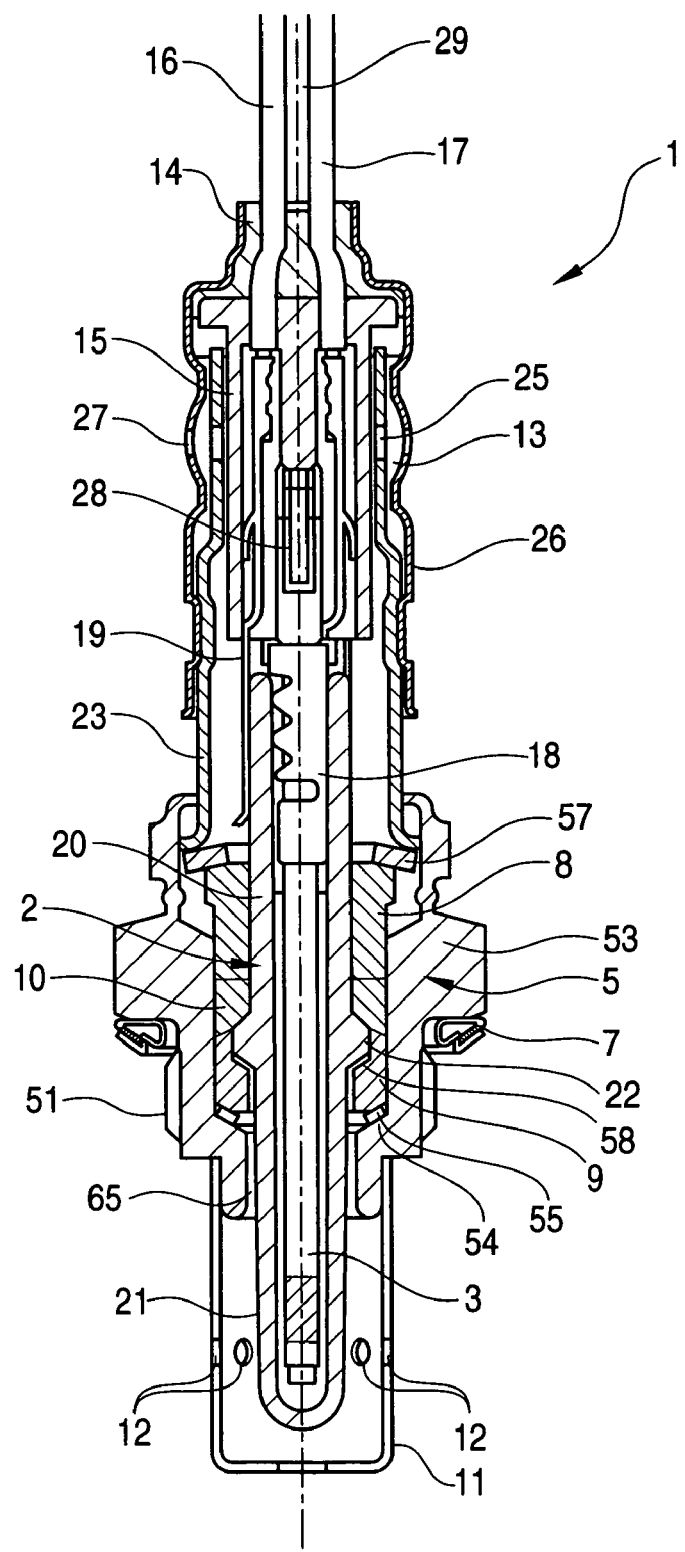
FIG. 1 is a diagram showing the structure of an oxygen sensor according to an embodiment of the invention.

Reference numerals used to identify various structural elements in the drawings include the following:
1—OXYGEN SENSOR, 2—DETECTING ELEMENT, 3—HEATER, 5—METAL SHELL, 7—GASKET, 8, 9—INSULATOR, 10—POWDER LAYER, 11—PROTECTOR, 12—GAS PERMEATING HOLES, 13—FILTER, 14—GROMMET, 15—CERAMIC SEPARATOR, 16, 17, 29—LEAD WIRE, 18—INNER ELECTRODE CONNECTING FITTING, 19—OUTER ELECTRODE CONNECTING FITTING, 20—ELEMENT BODY, 21—DETECTING PORTION, 22—FLANGE, 23—INNER CYLINDER MEMBER, 24—STEP, 25—GAS INLET HOLES, 26—OUTER CYLINDER MEMBER, 27—AUXILIARY GAS INLET HOLES, 28—HEATER CONNECTING TERMINAL, 30—OUTER ELECTRODE, 31—DETECTING ELECTRODE, 32—LEAD PORTION, 33—RING PORTION, 40—INSULATING LAYER, 50—PROTECTING LAYER, 51—THREAD, 52—HEXAGONAL PORTION, 53—BULGE, 54—FITTING SIDE STEP, 55, 58—PACKING, 56—ADDITIONALLY FASTENED PORTION, 57—ANNULAR RING, 60—INNER ELECTRODE, and 71—INSULATION RESISTANCE TESTER.

DETAILED DESCRIPTION OF THE INVENTION

An embodiment, in which a gas sensor of the invention is applied to an oxygen sensor, will be described with reference to the accompanying drawings. However, the prevent invention should not be construed as being limited thereto. FIG. 1 shows a schematic construction of the oxygen sensor according to one embodiment of the gas sensor of the invention.

As shown in FIG. 1, an oxygen sensor 1 is provided with a detecting element 2 as a gas detecting element, a heater 3, a metal shell 5 and other components. Of these, the heater 3 is made from a rod-shaped ceramic heater and is inserted into the detecting element 2.

The metal shell 5 is equipped in its outer circumference with a thread 51 for mounting the oxygen sensor 1 on the mounting portion of an exhaust pipe or the like and with a bulge 53, to which a mounting fitting is applied when the sensor is mounted on the mounting portion of the exhaust pipe. Here, the bulge 53 is equipped with a gasket 7 on its leading end face.

The metal shell 5 is equipped on its inner circumference with a fitting side step 54 which is radially reduced toward the leading end side. Interposed between the metal shell 5 and the detecting element 2, moreover, are insulators 8 and 9 made from insulating ceramics. A powder layer 10 of talc or the like is sandwiched under compression between insulators 8 and 9. This powder layer 10 seals the gap between the detecting element 2 and the metal shell 5 to retain gas-tightness. A packing 55 is sandwiched between the leading end of the insulator 9 and the fitting side step 54, and an annular ring 57 is provided at the rear end of the insulator 8.

To the leading end side of the metal shell 5, a protector 11 is attached for covering a detecting portion 21 of the detecting element 2. This protector 11 is provided with a plurality of gas permeating holes 12 for introducing the gas to be measured.

To the rear end side of the metal shell 5, moreover, an inner cylinder member 23 is attached which is made of SUS304L. The inner cylinder member 23 is provided with gas inlet holes 25 for introducing a reference gas into the gas detecting element.

On the outer side of the inner cylinder member 23, an outer cylinder member 26 is provided, which is equipped with a plurality of auxiliary gas inlet holes 27 at positions corresponding to the gas inlet holes 25. Between the gas inlet holes 25 and the auxiliary gas inlet holes 27, moreover, a filter 13 is formed for covering the gas inlet holes 25. The filter 13 is fixed by additionally fastening the outer cylinder member 26 on the leading end side and the rear end side of the auxiliary gas inlet holes 27. On the inner side of the inner cylinder member 23, a ceramic separator 15 is formed. This ceramic separator 15 is housed by connecting an outer electrode connecting fitting 19 for connection to an outer electrode 30, an inner electrode connecting fitting 18 for connection to an inner electrode 60, and a heater connecting terminal 28 for connection to the heater 3, respectively, with corresponding lead wires 16, 17 and 29. These lead wires 16, 17 and 29 are connected with the outside through a grommet 14 made of rubber, which is fixed on the rear end side of the outer cylinder member 26.

The aforementioned oxygen sensor 1 is used in a state, in which its leading end side (as located on the lower side of FIG. 1) from the thread 51 is positioned in an exhaust pipe or the like and in which its rear end side (as located on the upper side of FIG. 1) from the same is positioned in the outside atmosphere. The detecting element 2 is heated and activated by the heater 3 arranged inside the detecting element 2. Moreover, the outside atmosphere (air), as a reference gas, is introduced into the detecting element 2 through the auxiliary gas inlet holes 27, the filter 13 and the gas inlet holes 25 in the recited order. The exhaust gas is introduced to the outside of the detecting element 2 through the gas permeating holes 12 of the protector 11.

As a result, an oxygen concentration electromotive force is generated according to a difference in oxygen concentration between the inner and outer faces of the detecting element 2. Moreover, the oxygen concentration in the exhaust gas is detected by extracting the oxygen concentration electromotive force as a detection signal of the oxygen concentration in the exhaust gas through the inner electrode 60, the inner electrode connecting fitting 18 and the lead wire 17, and through the outer electrode 30, the outer electrode connecting fitting 19 and the lead wire 16.

Next, the detecting element 2 is described with reference to FIGS. 2 to 4.

Figure 2:
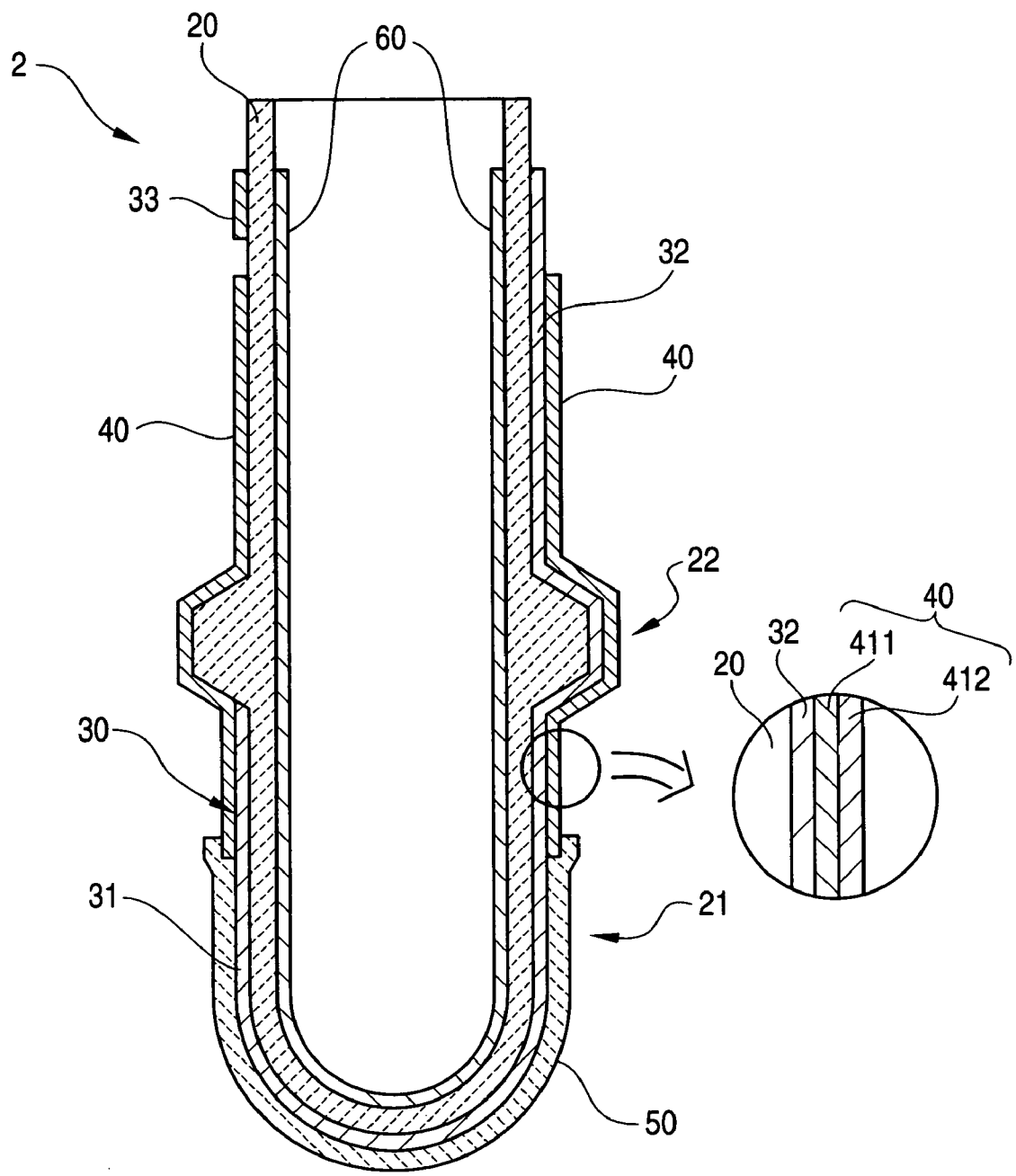
FIG. 2 is a diagram showing a sectional portion of the oxygen sensor of FIG. 1.

The detecting element 2 is equipped, as shown in FIG. 2, with an element body (or substrate) 20 of a bottomed cylindrical shape having its leading end closed. This element body 20 is made from an oxygen ion conductive solid electrolyte member mainly made from zirconia or the like. Moreover, the element body 20 is equipped on the rear end side (as located on the upper side of FIG. 2) with a flange 22 protruding radially outward. Flange 22 is fixed, as shown in FIG. 1, on the insulator 9 through a packing 58. In FIG. 2, the sectional laminar structure of the detecting element 2 is schematically shown at an aspect ratio different from that of FIG. 1.

On the inner side of the element body 20, moreover, an inner electrode 60 is provided, which is made of porous Pt or a Pt alloy, for example. On the outer side of the element body 20, the outer electrode 30 is formed, which is made of porous Pt or a Pt alloy, for example. On the outer side of a detecting electrode 31, a protecting layer 50 is formed, which is a sprayed layer of a ceramic such as spinel.

Figure 3:
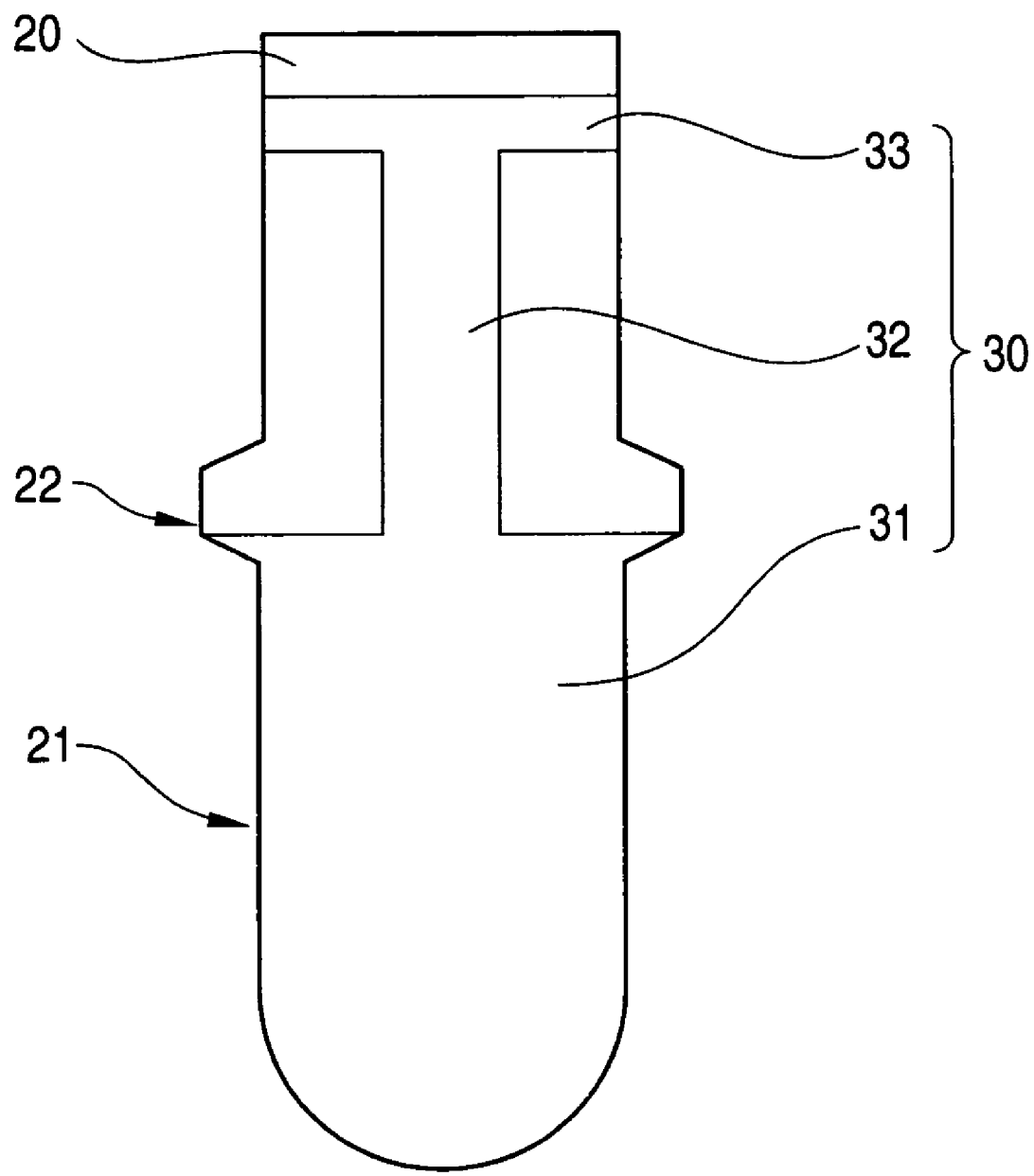
FIG. 3 is a diagram illustrating the structure of a detecting element of the oxygen sensor of FIG. 1.

This outer electrode 30 is constructed, as shown in FIG. 3, of the detecting electrode 31 formed to cover the section of the detecting portion 21 substantially, a lead portion 32 electrically connected to the detecting electrode 31 for extracting the electrode to the rear end side, and a ring portion 33. Over the entire area, from the rear end side portion of the detecting electrode 31 to the front of the ring terminal portion 33 of the lead portion 32, as shown in FIG. 2 and FIG. 4, an insulating layer 40 is formed so as to cover their outer side.

The insulating layer 40 which is a characteristic feature of the invention is described as follows. The insulating layer 40 is interposed between the powder layer 10 and the portion of the lead portion 32 covered by the powder layer 10. As a result, this structure keeps the outer electrode 30 (mainly the lead portion 32) and the powder layer 10 from direct contact. By employing this structure, even if the powder layer 10 absorbs moisture, the portion of the lead portion 32 (i.e., the portion of lead portion 32 covered by the powder layer 10) is covered by the powder layer 10 via the insulating layer 40 so that direct contact between the lead portion 32 and the powder layer 10 is prevented. As a result, the requisite insulation properties are retained between the outer electrode 30 and the metal shell 5. Therefore, a short-circuit can be prevented between the metal shell and the lead portion, thus preventing noise from being introduced into the output and allowing for precise detection of gas concentration.

This insulating layer 40 desirably has good insulation properties and heat resistance. Thus, the insulating layer 40 preferably is mainly made of glass (preferably at not less than 80% by weight, e.g. 100% by weight in this embodiment). The insulating layer 40 can include ceramic fillers e.g. alumina at less than 20% by weight. This glass preferably has a low alkali metal element content so as not to cause a reduction in electrical insulation properties due to migration.

As shown in FIG. 2, moreover, the insulating layer 40 is formed of a plurality of layers. Specifically, the insulating layer 40 is formed of a first glass layer 411 and a second glass layer 412, which have identical components. Thus, the insulating layer 40 is formed of plural layers of the first glass layer 411 and the second glass layer 412, so that the insulating layer 40 can mainly be composed of glass having no pores, to thereby prevent a reduction in electrical insulation properties when pores are present. Moreover, the insulating layer 40 is crystallized, after being formed, to have a raised softening temperature so as to be hardly softened when the second glass layer 412 is to be formed. As a result, the second glass layer 412 can be formed of the same material as that of the first glass layer 411, to thereby thicken the insulating layer 40 and prevent a reduction in insulation properties.

Moreover, this insulating layer 40 extends so far as to be between the packing 58 and the flange 22. As a result, even if a portion of the powder layer 10 permeates to the rear end side of packing 58, it is possible to prevent a short-circuit, as might otherwise occur due to moisture absorption, between the metal shell 5 and the detecting electrode 31.

Moreover, insulating layer 40 extends in the leading end direction farther than the leading end of the metal shell 5. When the gas sensor 1 is attached to an exhaust pipe or the like, carbon or the like in the gas to be measured enters the gap 65, as formed in the leading end direction farther than the packing 58, between the detecting element 2 and the metal shell 5. Even if the carbon adheres to the surfaces of the gas detecting element and the metal shell, the insulating layer 40 effectively prevents a short-circuit, as might otherwise be caused by the carbon having been adhered, between the metal shell 5 and the detecting electrode or the lead portion 32.

Figure 4:
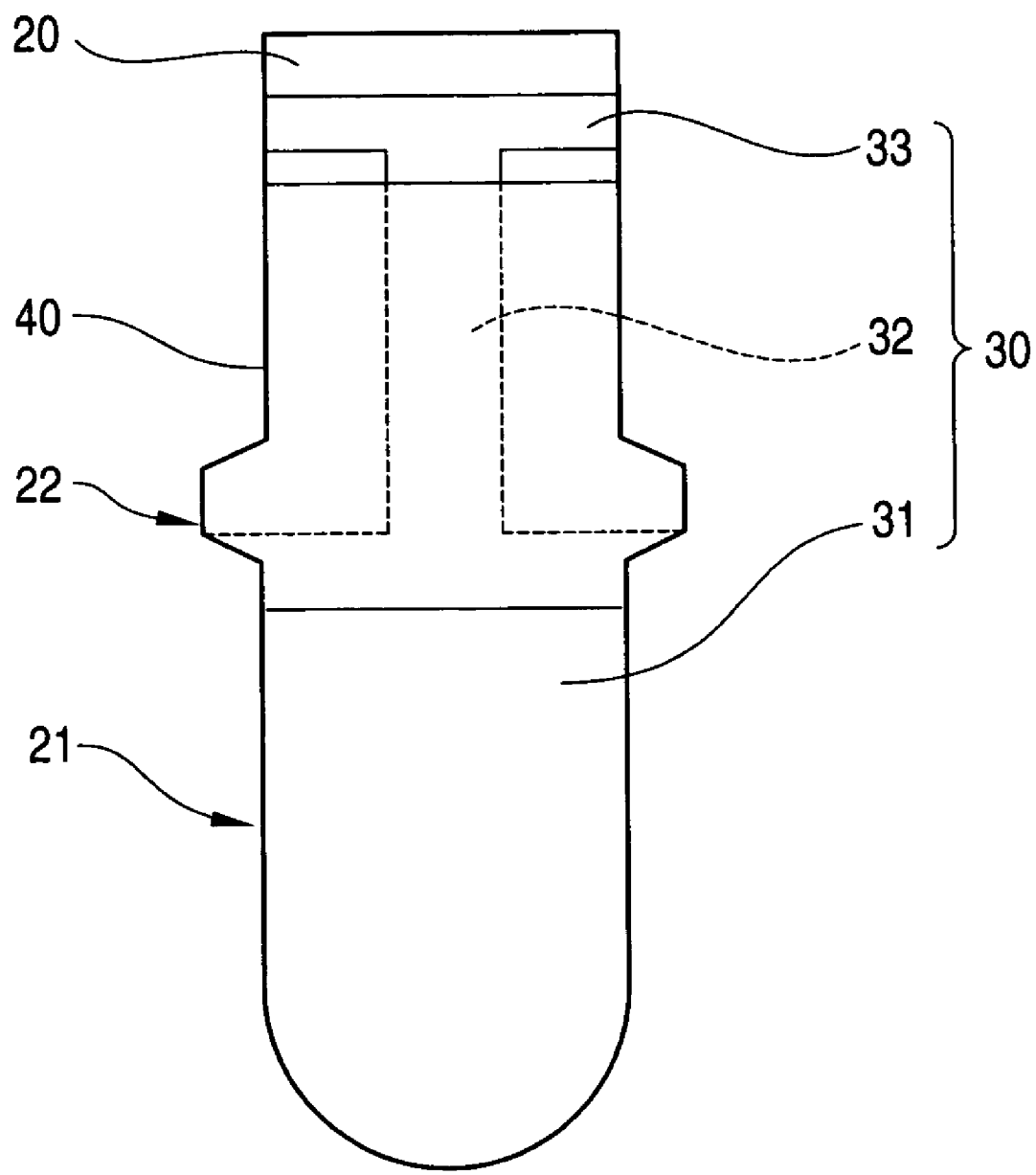
FIG. 4 is another diagram illustrating the structure of the detecting element of the oxygen sensor of FIG. 1.

Moreover, insulating layer 40 extends to the rear end of the detecting electrode 31, as shown in FIG. 4. As a result, it is possible to reliably prevent a short-circuit between the lead portions.

As shown in FIG. 2, the leading end side of the insulating layer 40 is covered with the protecting layer 50. As a result, the leading end side of the gas detecting element 2 at positions farther than the packing 58 is covered with either the protecting layer 50 or the insulating layer 40. Therefore, even if carbon or the like is deposited farther than the packing 58 in the leading end direction into the gap between the metal shell 5 and the gas detecting element 2 (so that the carbon or the like adheres to the metal shell 5 or the gas detecting element 2), electric current (leakage current) can be effectively prevented. In this regard, the protecting layer 50 or the insulating layer 40 prevents electric current from flowing between the metal shell 5 and the detecting electrode 31 or the lead portion 32. As such, output noise is avoided, allowing for precise gas concentration detection.

Especially, the protecting layer 50 covers the leading end portion of the insulating layer 40 so that the insulation property can be retained by the porous protecting layer 50 and the insulating layer 40.

Figure 5:
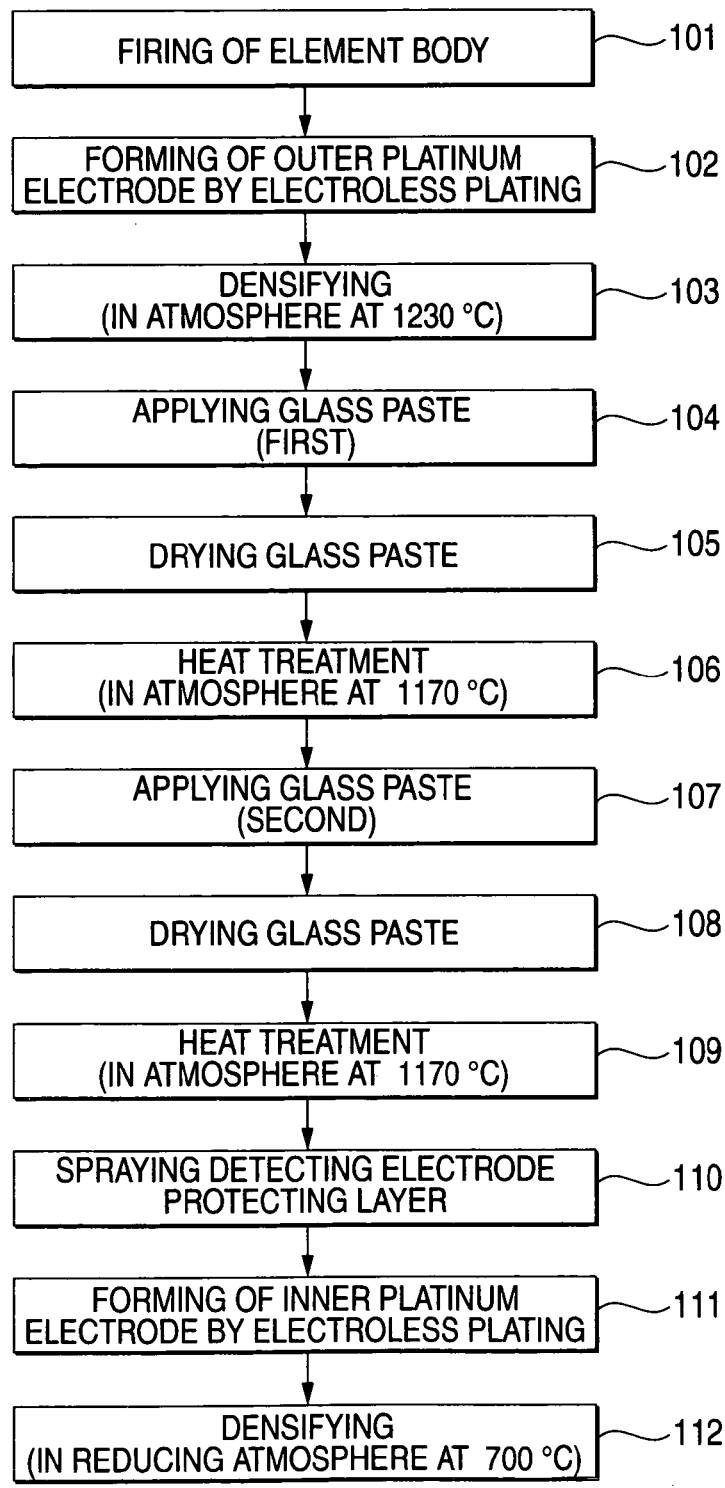
FIG. 5 is a flow chart of manufacturing steps for providing the detecting element.

Next, a method for manufacturing the detecting element 2 is described with reference to FIG. 5. As shown in FIG. 5, the substrate (the element body 20) which is made from an oxygen ion conductive solid electrolyte member or the like mainly composed of zirconia or the like is fired (at 101).

Next, the platinum electrode (the outer electrode 30) is formed (at 102) by electroless plating, and is densified (at 103) by heating. The heating is performed in air at a temperature of 1230° C.

Next, the portion forming the insulating layer 40 on the substrate outer side is subjected to a first glass paste application (at 104). For this glass paste application, the dip method can be used, for example, in which the element body is dipped in glass paste by masking the element body other than the glass paste applied portion with TEFLON (Registered Trade Name) tape or the like. In this case, the glass paste contents are at ratios of 10 to 15 g of powder glass, 10 ml of pure water, and 0.1 to 1.0 g of binder. It is also possible to use the roller method, in which glass paste is applied by bringing the element body into abutment against a roller while turning it in a direction opposite that of the roller, or the spray method, in which glass paste is sprayed on the element body while turning the element body.

Next, the glass paste is dried (at 105) by means of a heat gun or the like, and is then to heat treated using a muffle furnace or the like to form the first glass layer 411 (at 106). This heat treatment is performed in air at a temperature of 1170° C. for a time period of 20 minutes, for example.

Next, a second glass paste application is performed similar to the first to the aforementioned glass layer (at 107), and is then dried (at 108). After this, a heat treatment (e.g., in air at a temperature of 1170° C.) is conducted to form the second glass layer (at 109). The first glass layer 411 has been crystallized so that it is hardly softened even by the heat treatment at 1170° C. Thus, the insulating layer 40 is formed by applying the glass paste twice, so that the non-porous insulating layer 40 can be formed to prevent the insulation property from being lowered by pores, if any. The glass layer thus formed by these steps has a thickness of about 40 to 300 μm. If the thickness is less than 40 μm, sufficient insulation properties may not be obtained when operating the sensor.

Next, the protecting layer 50 is formed (at 110) by plasma spraying on the outer side of the detecting electrode 31. This protecting layer 50 is made from a ceramic porous layer of spinel or the like having a thickness of about 100 to 180 μm.

Next, the platinum electrode (the inner electrode 60) is formed (at 111) by an electroless plating, and is densified (at 103) by heating. The conditions for the densifying treatment are a reducing atmosphere of hydrogen or the like at a temperature of 700° C.

Then, the detecting element 2 having the inner electrode 60 formed therein is held by a known method on the metal shell 5 through the packing 58 and the insulator 9, and is interior-finished by the powder layer 10, the insulator 8 and the annular ring 57 in the recited order. The inner cylinder member 23 is additionally fastened at its leading end portion by the rear end portion of the metal shell 5. After this, the outer cylinder member 26, the filter 13, the grommet 14 and so on are mounted to complete the oxygen sensor 1.

Figure 6:
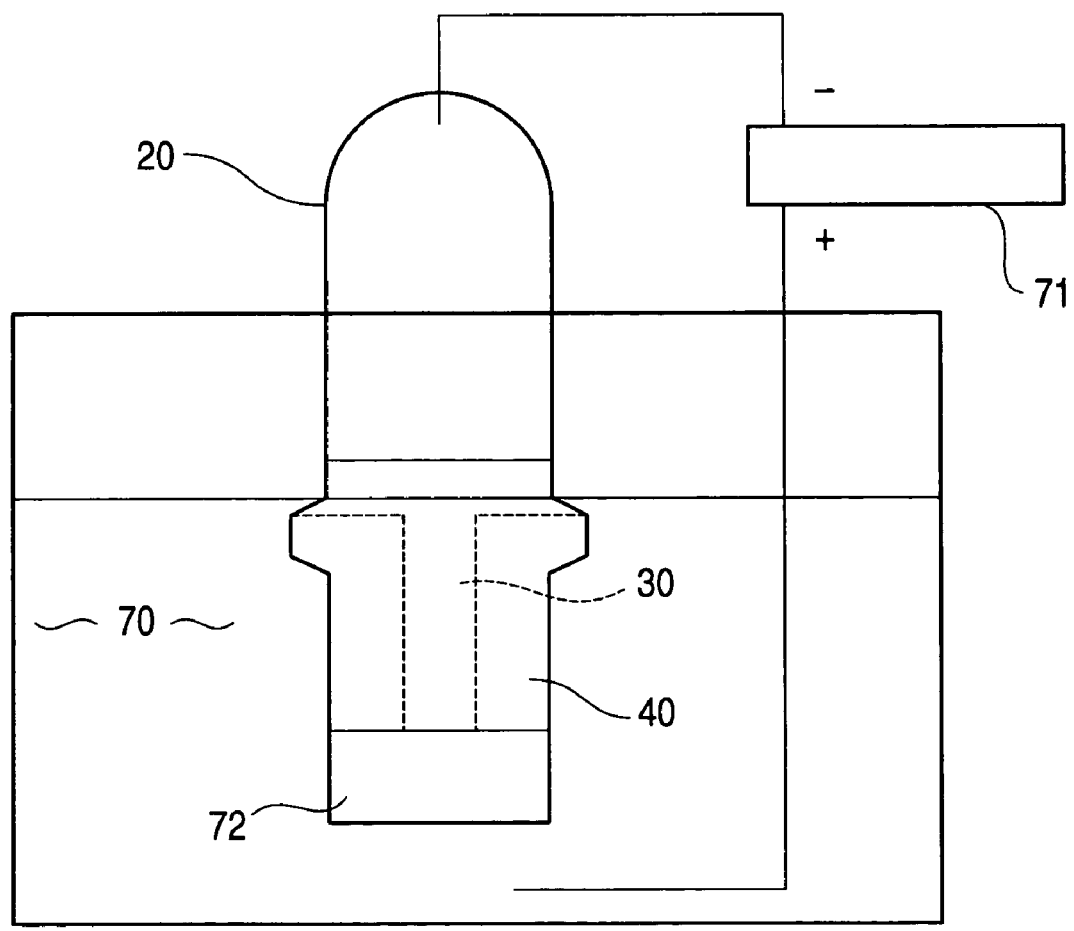
FIG. 6 is a diagram illustrating a method for conducting an underwater insulation test of an insulating layer.

Next, the insulating layer 40 thus formed by the aforementioned manufacturing steps was subjected to an underwater insulation test. Specifically, the element body 20 having the outer electrode 30 and the insulating layer 40 formed thereon was dipped in city water 70, as shown in FIG. 6, and the underwater insulation tests were conducted by measuring the insulation resistances with an insulation resistance tester 71. Here, that portion of the element body 20 which did not have the insulating layer 40 on the rear end side (as located on the lower side of FIG. 6) was insulated by winding an insulating tape 72 of silicone. The underwater insulation tests were conducted by applying a DC voltage of 500 V and measuring the insulation resistances after charging for 10 seconds. As a result, the insulation resistance was about 5000 MΩ for the insulating layer 40 formed by the aforementioned manufacturing steps.

For practical use, the insulation resistance of the insulating layer 40 is sufficient if it has a value of about 15 MΩ. At a minimum value of about 5 MΩ, current flow can be suppressed to 1 μA or less to thereby to suppress the occurrence of noise. Therefore, the insulation resistance of the insulating layer 40 formed by the aforementioned measuring method is preferably 5 MΩ or higher, and more preferably 15 MΩ or higher.

Practically, the oxygen sensor 1 having the insulating layer 40 formed to a thickness of 70 μm was prepared, as a First Example, with crystallized glass containing 45 wt. % of $SiO_2$, 16 wt. % of $Al_2O_3$, 15 wt. % of BaO, 10 wt. % of ZnO, 9 wt. % of CaO and 0.5 wt. % of $Na_2O$. Then, this oxygen sensor 1 was moistened in an environment of a temperature of 60° C. and a humidity of 95% for 60 hours. After this, the insulation resistances were measured to be about 100 MΩ or more even immediately after being moistened. As a Comparative Example, on the other hand, similar measurements were conducted by the oxygen sensor 1 not having the insulating layer 40, and the insulating resistance was about 0.01 MΩ or less.

As a Second Example, the oxygen sensor 1 having the insulating layer 40 formed to a thickness of 70 μm was likewise prepared with amorphous glass containing 29 wt. % of $SiO_2$, 54 wt. % of BaO, 4 wt. % of CaO, 3 wt. % of $B_2O_3$, and 0.5 wt. % of $Na_2O$. Then, this oxygen sensor 1 was moistened in an environment of a temperature of 60° C. and a humidity of 95% for 60 hours. After this, the insulation resistances were measured to be about 200 MΩ or more even immediately after being moistened. As a Comparative Example, on the other hand, similar measurements were conducted by the oxygen sensor 1 not having the insulating layer 40, and the insulating resistance was about 0.01 MΩ or less.

Likewise, as a Third Example, the oxygen sensor 1 having the insulating layer 40 formed to a thickness of 70 μm was prepared with crystallized glass containing 32 wt. % of $SiO_2$, 16 wt. % of $Al_2O_3$, 19 wt. % of CaO, 25 wt. % of ZnO, 10 wt. % of $TiO_2$, 0.1 wt. % of $Na_2O$ and 0.04 wt. % of $K_2O$. Then, this oxygen sensor 1 was moistened in an environment of a temperature of 60° C. and a humidity of 95% for 60 hours. After this, the insulation resistances were measured to be about 100 MΩ or more even immediately after being moistened. As a Comparative Example, on the other hand, similar measurements were conducted by the oxygen sensor 1 not having the insulating layer 40, and the insulating resistance was about 0.01 MΩ or less.

As described above, the examples of the invention could maintain insulating resistances 1,000 times as high as that of the oxygen sensor 1 of the prior art, and accordingly, provide an insulation property sufficient for suppressing the occurrence of noise.

The insulating layer 40 is not to be construed as being limited to the above-specified materials, but may be made from any material so long as the material has an insulating resistance, preferably of 5 MΩ or higher, and more preferably of 15 MΩ or higher. Moreover, the insulating layer 40 can likewise be applied not only to the aforementioned oxygen sensor 1, but also to a gas sensor for detecting another kind of gas.

Moreover, the above described method of the embodiment is one in which the first glass layer 411 and the second glass layer 412 are formed, but the glass components can be changed between the first glass paste application and the second glass paste application. In a case where the first glass layer is not crystallized, the second glass layer is preferably formed using a glass paste having a lower softening point than that of the first glass layer. By using a glass paste for the first glass layer having a higher softening point than that of the glass plate, moreover, the second glass layer can be formed by setting the second heat treatment temperature higher, within a range for maintaining the film thickness of the first glass layer, than that of the first heat treatment temperature. In this case, it is possible to improve adhesion between the first glass layer and the second glass layer.

It should further be apparent to those skilled in the art that various changes in form and detail of the invention as shown and described above may be made. It is intended that such changes be included within the spirit and scope of the claims appended hereto.

This application is based on Japanese Patent application JP 2004-346331, filed Nov. 30, 2004, and Japanese Patent application JP 2005-302311, filed Oct. 17, 2005 the entire contents of which are hereby incorporated by reference, the same as if set forth at length.

What is claimed is:

1. A gas sensor comprising:
    a gas detecting element extending in an axial direction and including a detecting electrode provided on an outer surface of a leading end side of said gas detecting element, and a lead portion connecting to said detecting electrode and extending toward a rear end side of said gas detecting element;
    a cylindrical metal shell housing said gas detecting element such that said gas detecting element protrudes from a leading end side of said metal shell;
    a powder layer filling a gap between said gas detecting element and said metal shell and covering at least a portion of said lead portion; and
    an insulating layer provided so as to prevent direct contact between said powder layer and the gas detecting element,
    wherein said gas detecting element includes a porous protecting layer formed on the gas detecting element so as to cover at least a portion of said detecting electrode and overlapping at least a leading end portion of said insulating layer,
    wherein the insulating layer comprises glass, and
    wherein the insulating layer is not present at a distal end of the gas detecting element.

2. The gas sensor as claimed in claim 1, wherein said insulating layer includes a plurality of layers.

3. The gas sensor as claimed in claim 2, wherein said plurality of layers includes a first insulating layer arranged adjacent to said lead portion, and said first insulating layer comprises crystallized glass.

4. The gas sensor as claimed in claim 1, further comprising a packing provided farther than said powder layer in a leading end direction, wherein said gas detecting element includes a flange bulging to a radially outer side and contacting said packing; and said insulating layer extends to cover a portion of said flange contacting said packing.

5. The gas sensor as claimed in claim 1, wherein said protecting layer covers a leading end portion of said insulating layer.

6. The gas sensor as claimed in claim 1, wherein said insulating layer extends beyond a leading end of said metal shell in a leading end direction.

7. A method for manufacturing the gas sensor as claimed in claim 1, the method comprising forming said insulating layer by at least:
    applying a glass paste;
    drying said glass paste; and
    heat-treating said glass paste.

8. The method as claimed in claim 7, wherein a series of steps including said applying, said drying and said heat treating steps are repeated at least two times to form said insulating layer.

* * * * *